US009642542B2

(12) United States Patent
Sawanoi et al.

(10) Patent No.: US 9,642,542 B2
(45) Date of Patent: *May 9, 2017

(54) METHOD AND APPARATUS FOR MEASURING AND DISPLAYING BLOOD PRESSURE

(71) Applicant: OMRON HEALTHCARE Co., Ltd., Kyoto (JP)

(72) Inventors: Yukiya Sawanoi, Nara (JP); Mika Ezoe, Osaka (JP); Ayako Sakano, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 838 days.

This patent is subject to a terminal disclaimer.

(21) Appl. No.: 14/012,144

(22) Filed: Aug. 28, 2013

(65) Prior Publication Data

US 2015/0065895 A1    Mar. 5, 2015

(51) Int. Cl.
*A61B 5/0225* (2006.01)
*A61B 5/024* (2006.01)
*A61B 5/11* (2006.01)

(52) U.S. Cl.
CPC ......... *A61B 5/0225* (2013.01); *A61B 5/024* (2013.01); *A61B 5/1117* (2013.01)

(58) Field of Classification Search
CPC ......... A61B 5/022; A61B 5/024; A61B 5/742; A61B 5/7282; A61B 5/0225; A61B 5/02405; A61B 5/1117
USPC ............................ 600/301, 490, 493, 485
See application file for complete search history.

(56) References Cited

U.S. PATENT DOCUMENTS 9,314,171 B2 *   4/2016 Ezoe .................. A61B 5/022
9,314,211 B2 *   4/2016 Ezoe .................. A61B 5/7282
2004/0097815 A1 * 5/2004 Forstner .............. A61B 5/022
                                                                 600/485

FOREIGN PATENT DOCUMENTS

EP          1101440 A1 *  5/2001   ............. A61B 5/021

OTHER PUBLICATIONS

Rossmax Hemodynamic Stability Determination (HSD). Rossmax International Ltd., n.d. (2 pages) Nov. 18-21, 2009 http://www.medica.de/.

* cited by examiner

*Primary Examiner* — Gary Jackson
*Assistant Examiner* — Boniface N Nganga
(74) *Attorney, Agent, or Firm* — Osha Liang LLP

(57) ABSTRACT

A blood pressure measurement device measures blood pressure and a blood pressure change affecting factor of a patient. The device includes a memory, a tolerance determination section, and a display unit. The tolerance determination section includes a rest/unrest condition determination section and a blood pressure tolerance determination section. The tolerance determination section determines whether the blood pressure of the patient is tolerant to the blood pressure change affecting factor. The display unit of the device displays the measured blood pressure, the measured blood pressure change affecting factor, and a tolerance determination of the patient.

12 Claims, 3 Drawing Sheets

|  |  | systolic | diastolic | heart rate | pulse period change (sec) |
|---|---|---|---|---|---|
| Patient A | 1) | 120 | 83 | 81 | 0.032 |
|  | 2) | 127 | 87 | 86 | 0.032 |
|  | 3) | 126 | 87 | 76 | 0.036 |
|  | 1,2,3 Ave | 124 | 86 | 81 | 0.033 |
|  | 4) | 161 | 97 | 101 | 0.104 |
| Patient B | 5) | 129 | 87 | 88 | 0.032 |
|  | 6) | 127 | 88 | 88 | 0.030 |
|  | 7) | 126 | 87 | 88 | 0.048 |
|  | 5,6,7 Ave | 127 | 87 | 88 | 0.037 |
|  | 8) | 134 | 92 | 98 | 0.084 |

*FIG. 3*

Patient: A
Systolic Blood Pressure: 120
Diastolic Blood Pressure: 83
Heart Rate: 81
Rest or Unrest? Rest
Tolerance: Not Available Patient: A
Systolic Blood Pressure: 161
Diastolic Blood Pressure: 97
Heart Rate: 101
Rest or Unrest? Unrest
Tolerance: No

METHOD AND APPARATUS FOR MEASURING AND DISPLAYING BLOOD PRESSURE

BACKGROUND (1) Field of the Invention

The present invention relates to a blood pressure measurement device and a method for measuring and displaying blood pressure. More specifically, the present invention relates to apparatus and methods for measuring and displaying a tolerance to a blood pressure change affecting factor of a patient.

(2) Description of Related Art

A rest condition of a patient is important when measuring blood pressure. If a patient is not in a rest condition, the measured blood pressure may differ from the value measured in the rest condition. Thus, it is necessary to determine whether a patient was in the rest condition when the blood pressure is being measured.

As a measure to determine whether a patient was in the rest condition, measuring heart rate and pulse wave period is known. Generally, a patient's pulse wave period becomes short or unstable after hard exercise or mental distress. Therefore, it is possible to determine whether a patient was in a rest condition by examining whether the patient's pulse wave period was stable during a certain period of time.

Rossmax Hemodynamic Stability Determination (HSD) measures a user's pulse period of blood pressure. When the pulse period is short or unstable, the Rossmax HSD determines that the user is in an unrest condition (HSD positive), and displays the determination together with the measured blood pressure. If the pulse period is more than a certain interval period and stable, the Rossmax HSD determines that the user is in a rest condition (HSD negative), and displays the determination together with the measured blood pressure.

However, for some people, the change of the pulse wave period has little influence on the blood pressure value. Those people have a high tolerance to a blood pressure change affecting factor. Depending on the tolerance to the blood pressure change affecting factor of the patient, the impact of the blood pressure change affecting factor to the blood pressure value is different.

Displaying a value of the blood pressure change affecting factor together with the measured blood pressure is unsatisfactory data to show whether the patient can decide whether the measured blood pressure is reliable.

As used in this disclosure, the term "blood pressure change affecting factor," may refer to the heart rate and the pulse interval period of the patient, in accordance with one or more embodiments of the present invention.

SUMMARY OF INVENTION

One or more embodiments of the present invention relate to a blood pressure measurement device that displays a tolerance to a blood pressure change affecting factor of a patient, the device comprising: means for measuring blood pressure and the blood pressure change affecting factor of the patient; a memory that stores the measured blood pressure and the blood pressure change affecting factor; a tolerance determination section that determines the tolerance of the patient to the blood pressure change affecting factor; the tolerance determination section further comprising: a rest/unrest condition determination section that: compares the measured blood pressure change affecting factor with a predetermined standard value; determines that the patient is in a rest condition if a difference between the measured blood pressure change affecting factor and the predetermined standard value is less than or equal to a predetermined threshold value; and determines that the patient is in an unrest condition if the difference between the measured blood pressure change affecting factor and the predetermined standard value is greater than the predetermined threshold value; a blood pressure tolerance determination section that: determines that the blood pressure of the patient is tolerant to the blood pressure change affecting factor if the difference between the blood pressure in the rest condition and the blood pressure in the unrest condition is less than a predetermined value; and determines that the blood pressure of the patient is not tolerant to the blood pressure change affecting factor if the difference between the blood pressure in the rest condition and the blood pressure in the unrest condition is equal to or more than the predetermined value; and a display unit that displays the measured blood pressure, the measured blood pressure change affecting factor, and a tolerance determination of the patient.

One or more embodiments of the present invention relate to a blood pressure measurement device that displays a tolerance to a blood pressure change affecting factor of a patient, the device comprising: a cuff having an air bladder, wherein the cuff is configured to be wrapped around a measurement site of the patient; a measurement air system comprising a pressure sensor, a pump, and a valve; an air tube that connects the air bladder of the cuff to the measurement air system; a blood pressure calculation section that calculates a blood pressure of the patient based on an internal pressure of the air bladder as detected by the pressure sensor; a blood pressure change affecting factor calculation section that measures the blood pressure change affecting factor of the patient based on a detected pulse wave waveform; a memory that stores the calculated blood pressure and the blood pressure change affecting factor; a tolerance determination section that determines the tolerance of the blood pressure of the patient to the blood pressure change affecting factor, the tolerance determination section further comprising: a rest/unrest condition determination section that: compares the measured blood pressure change affecting factor with a predetermined standard value; determines that the patient is in a rest condition if a difference between the measured blood pressure change affecting factor and the predetermined standard value is less than or equal to a predetermined threshold value; and determines that the patient is in an unrest condition if the difference between the measured blood pressure change affecting factor and the predetermined standard value is greater than the predetermined threshold value; a blood pressure tolerance determination section that: determines that the blood pressure of the patient is tolerant to the blood pressure change affecting factor if the difference between the blood pressure in the rest condition and the blood pressure in the unrest condition is less than a predetermined value; and determines that the blood pressure of the patient is not tolerant to the blood pressure change affecting factor if the difference between the blood pressure in the rest condition and the blood pressure in the unrest condition is equal to or more than the predetermined value; and a display unit that displays the measured blood pressure, the measured blood pressure change affecting factor, and a tolerance determination of the patient.

One or more embodiments of the present invention relate to method for measuring and displaying blood pressure using a blood pressure measurement device comprising a processor, a memory, and a display, the method comprising the steps of: measuring the blood pressure of a patient together with a blood pressure change affecting factor; when a difference between the blood pressure change affecting factor and a standard value of the blood pressure change affecting factor is less than or equal to a predetermined threshold value, determining that the blood pressure of the patient is measured under a rest condition, and storing the blood pressure as being measured under the rest condition in the memory; when the difference between the blood pressure change affecting factor and the standard value of the blood pressure change affecting factor is greater than the predetermined threshold value, determining that the blood pressure of the patient is measured under an unrest condition, and comparing the blood pressure of the patient measured under the unrest condition with the blood pressure of the patient measured under the rest condition stored in the memory; determining that the blood pressure of the patient is tolerant to the blood pressure change affecting factor if the difference between the blood pressure of unrest condition and the blood pressure of rest condition is less than a predetermined value; determining that the blood pressure of the patient is not tolerant to the blood pressure change affecting factor if the difference between the blood pressure of unrest condition and the blood pressure of rest condition is equal to or more than a predetermined value; and displaying the measured blood pressure, the blood pressure change affecting factor, and a tolerance determination on the display of the blood pressure measurement device.

BRIEF DESCRIPTION OF DRAWINGS

FIG. 3 is an example of a data table that shows the blood pressure measurements, heart rates, and pulse period changes of Patient A and Patient B according to one or more embodiments of the present invention.

FIGS. 4(A) and 4(B) are example displays of the data shown in FIG. 3 according to one or more embodiments of the present invention.

DETAILED DESCRIPTION OF INVENTION

Figure 1:
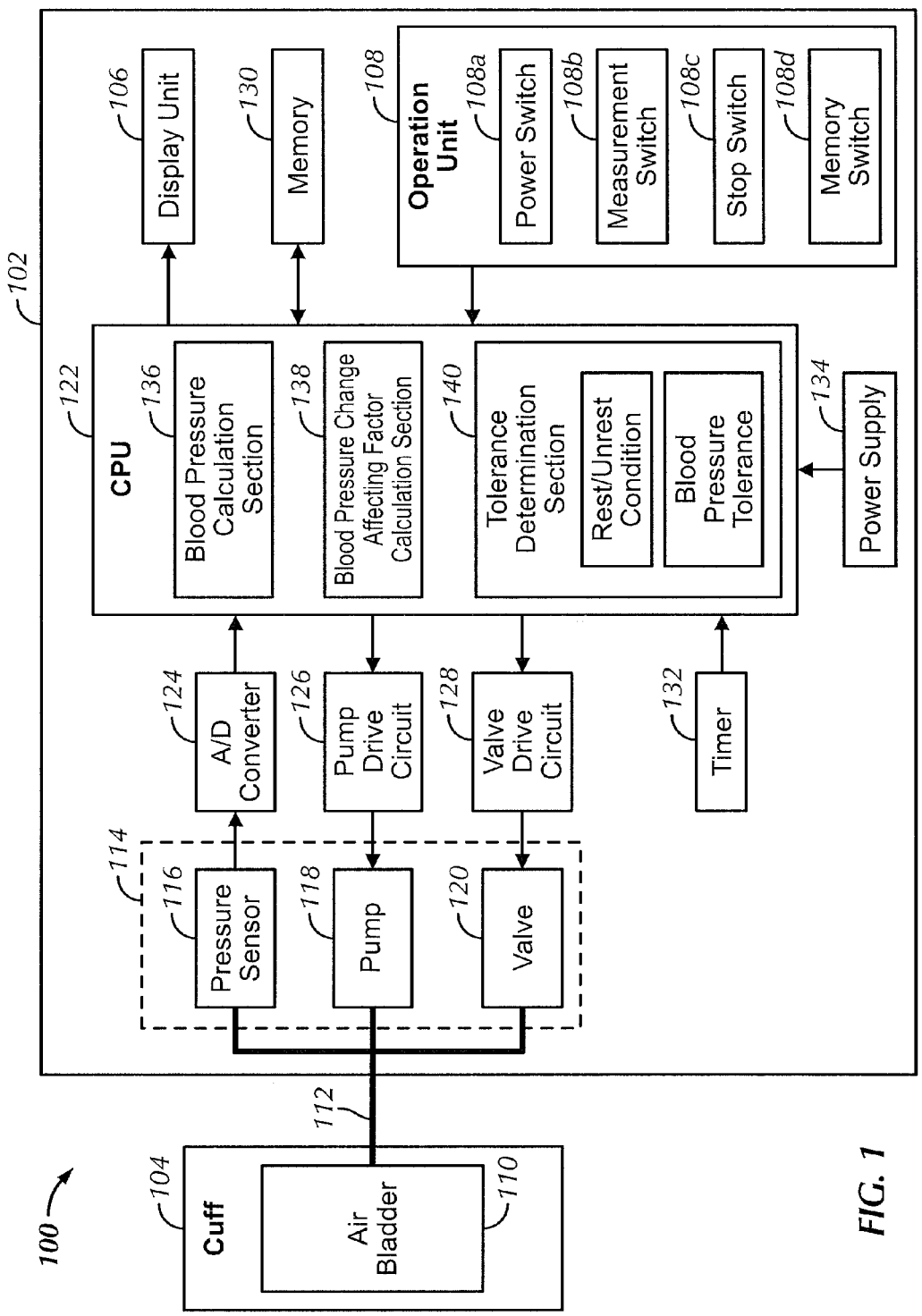
FIG. 1 is a functional block diagram showing a configuration of a blood pressure measurement device (sphygmomanometer) according to one or more embodiments of the present invention.

Hereinafter, embodiments of a blood pressure measurement device according to one or more embodiments of the present invention will be described with reference to the drawings. In the following description, the same reference numerals are given to the same components and constituent elements. The names and functions thereof are also the same.

FIG. 1 is a functional block diagram showing a configuration of a blood pressure measurement device (sphygmomanometer) according to one or more embodiments of the present invention.

Referring to FIG. 1, the blood pressure measurement device (sphygmomanometer) 100 is provided with a device main body 102 and a cuff 104. When blood pressure measurement is performed by the sphygmomanometer 100, the cuff 104, which has a belt-like outer shape, is wrapped around a measurement site of a patient. The cuff 104 houses an air bladder 110 serving as a fluid bag for compressing the measurement site.

The cuff 104 and the device main body 102 are connected by an air tube 112 serving as a connecting tube. According to one or more embodiments of the present invention, the air tube 112 consists of a flexible tube. One end of the air tube 112 is connected to a measurement air system 114 that is provided in the device main body 102. The other end of the air tube 112 is connected to the air bladder 110 of the cuff 104.

The measurement air system 114 supplies air to or discharges air from the air bladder 110 contained in the cuff 104 via air tube 112. The measurement air system 114 includes a pressure sensor 116 that detects the pressure inside the air bladder 110, and a pump 118 and a valve 120 for expanding and contracting the air bladder 110. The blood pressure measurement device (sphygmomanometer) 100 also includes a central processing unit (CPU) 122, an A/D converter 124, a pump drive circuit 126, and a valve drive circuit 128. The CPU 122 controls the entirety of the blood pressure measurement device (sphygmomanometer) 100. The A/D converter 124, the pump drive circuit 126, and the valve drive circuit 128 are connected to the measurement air system 114.

The pressure sensor 116 detects the internal pressure of the air bladder 110 and inputs a detection signal to the A/D converter 124. The input detection signal is converted to a digital signal by the A/D converter 124, and input to the CPU 122. The CPU 122 executes predetermined processing based on the internal pressure of the air bladder 110 obtained from the pressure sensor 116 and outputs control signals to the pump drive circuit 126 and the valve drive circuit 128 in accordance with the result of the predetermined processing.

The device main body 102 of the blood pressure measurement device (sphygmomanometer) 100 includes a memory 130, which stores programs executed by the CPU 122 and results of measurement. That is, the memory 130 is constituted by a storage medium. Memory 130 may be realized by a single storage medium or more than one storage media. Exemplary storage media include media for storing programs in a non-volatile manner such as CD-ROM (Compact Disc-Read Only Memory), DVD-ROM (Digital Versatile Disk-Read Only Memory), USB (Universal Serial Bus) memory, memory card FD (Flexible Disk), hard disk, magnetic tape, cassette tape, MO (Magnetic Optical Disc), MD (MiniDisc), IC (Integrated Circuit) card (excluding memory card), optical card, mask. ROM, EPROM, and EEPROM (Electronically Erasable Programmable Read-Only Memory).

The device main body 102 of the blood pressure measurement device (sphygmomanometer) 100 also includes a display unit 106 and an operation unit 108. The display unit 106 displays the results of measuring blood pressure values, heart rates, states of rest or unrest, tolerances, etc. using numerical values, labels, indicia, graphs, and the like in a manner that allows visible confirmation. A liquid crystal panel or the like, for example, may be used as this display unit 106. According to one or more embodiments of the present invention, the operation unit 108 includes a power switch 108a, a measurement switch 108b, a stop switch 108c, and a memory switch 108d.

The device main body 102 of the blood pressure measurement device (sphygmomanometer) 100 also includes a timer 132 and a power supply 134. The timer 132 has a clock function, and the power supply 134 supplies power to the CPU 122. According to one or more embodiments of the present invention, the power supply 134 supplies power to the CPU 122 from an external power supply. According to other embodiments of the present invention, the power supply 134 may be a battery or similar element that supplies power to the CPU 122 without receiving power from an external power supply.

As previously described, the operation unit 108 includes the power switch 108a, the measurement switch 108b, the stop switch 108c, and the memory switch 108d according to one or more embodiments of the present invention. The power switch 108a receives input of an instruction for turning the power supply on or off. The measurement switch 108b receives a measurement start instruction. The stop switch 108c receives a measurement stop instruction. Finally, the memory switch 108d receives an instruction to read out information such as blood pressure recorded in memory 130.

The CPU 122 includes a blood pressure calculation section 136 that calculates blood pressure values (a systolic blood pressure value, a diastolic blood pressure value, and/or an average blood pressure value) based on the internal pressure of the air bladder 110 obtained from the pressure sensor 116. The CPU 122 outputs the blood pressure values calculated by the blood pressure calculation section 136 to the display unit 106 to display them as a result of measurement.

The CPU 122 also includes a blood pressure change affecting factor calculation section 138. The blood pressure change affecting factor calculation section 138 measures the blood pressure change affecting factor, which is the heart rate and pulse interval period of a patient based on a detected pulse wave waveform. The CPU 122 outputs the heart rate and pulse interval period measured by the blood pressure change affecting factor calculation section 138 to the display unit 106 to display the heart rate and the pulse interval period as a result of measurement.

The CPU 122 also includes a tolerance determination section 140, which further includes a rest/unrest condition determination section and a blood pressure tolerance determination section. The rest/unrest condition determination section of the tolerance determination section 140 determines whether the patient is in a rest condition or an unrest condition during blood pressure measurement by comparing the measured heart rate or pulse interval period of the patient with a standard value thereof that is stored in the memory 130. If it is determined that the patient was in a rest condition during blood pressure measurement, the measured blood pressure is stored in the memory 130, and displayed on the display unit 106. If it is determined that the patient was in an unrest condition during blood pressure measurement, the blood pressure tolerance determination section of the tolerance determination section 140 determines whether the blood pressure of the patient is tolerant to the unrest condition by comparing the blood pressure measured in the unrest condition with the blood pressure measured in the rest condition, which is stored in the memory 130. The determination of whether the blood pressure of the patient is tolerant to the unrest condition may be displayed on the display unit 106.

Displaying the determination of whether the blood pressure of the patient is tolerant to the unrest condition on the display unit 106 together with the measured blood pressure of the patient allows the patient to decide whether the measured blood pressure is reliable.

Figure 2:
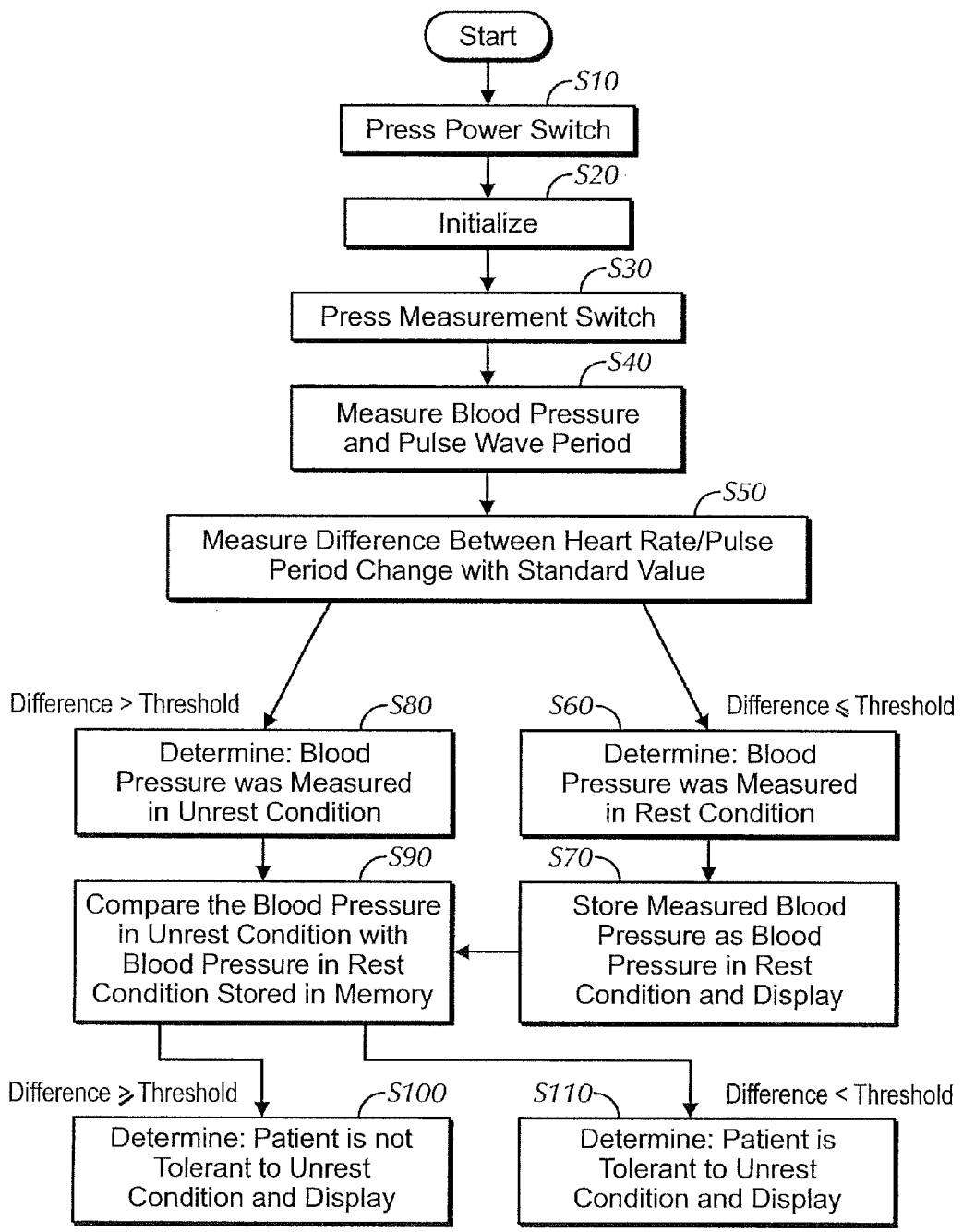
FIG. 2 is a flow chart of processing related to the determination of a patient's tolerance to a blood pressure change affecting factor in a blood pressure measurement device (sphygmomanometer) according to one or more embodiments of the present invention.

FIG. 2 is a flow chart of processing related to the determination of a patient's tolerance to a blood pressure change affecting factor in the blood pressure measurement device (sphygmomanometer) 100 according to one or more embodiments of the present invention. In the blood pressure measurement device (sphygmomanometer) 100, this processing is realized by the CPU 122 executing a program stored in the memory 130 (or in a recording medium detachable from the device main body 110).

Referring to FIG. 2, in the blood pressure measurement processing, first at step S10, the CPU 122 stands by until the power switch 108a is operated, and advances the processing to step S20 when it is judged that the power switch 108a has been operated.

At step S20, the CPU 122 initializes the blood pressure measurement device (sphygmomanometer) 100. The internal pressure of the air bladder 110 of the cuff 104 is thereby initialized.

At step S30, the CPU 122 stands by until the measurement switch 108b is operated. When it is judged that the measurement switch 108b has been operated, the CPU 122 advances the processing to step S40.

At step S40, the CPU 122 performs processing to measure the blood pressure (e.g., a systolic blood pressure value, a diastolic blood pressure value, and/or an average blood pressure value) and pulse wave period of the patient. The CPU 122 then advances the processing to step S50.

At step S50, the CPU 122 performs processing to compare the measured heart rate or pulse period of the patient with a standard value thereof that is stored in memory 130. According to one or more embodiments of the present invention, the "standard value" may be set based on an average heart rate or a change of pulse period of a person who is in a rest condition. For example, in the case of a heart rate, the standard value may be set as 80 beats/minute. In the case of a pulse period change, a difference between a maximum pulse period and a minimum pulse period in one measurement may be set as 0.04 sec as a standard pulse period change. As known by persons of ordinary skill in the art, a pulse period change of 0.04 sec is common for many people. According to one or more embodiments of the present invention, the average heart rate or pulse period change of the patient measured in the past measurements may be as the standard value in rest condition.

If the difference between the measured heart rate or pulse period change and its standard value is greater than a "threshold value," the CPU 122 advances the processing to S80, and it is determined that the patient was in an unrest condition at the time of measurement. On the other hand, if the difference between the measured heart rate or pulse period change and its standard value is less than or equal to the threshold value, the CPU 122 advances the processing to S60, and it is determined that the patient was in a rest condition at the time of measurement. The threshold value may be set appropriately by user. For example, according to one or more embodiments of the present invention, the threshold value may be set at 10 beats/minute for the heart rate, or 0.02 sec/measurement for the pulse period change.

At S70, the blood pressure (e.g., systolic blood pressure, diastolic blood pressure) is stored in the memory 130 as the blood pressure in a rest condition of the patient and will be displayed as such on the display unit 106. Data of blood pressure in a rest condition of the patient stored in the memory 130 will be read out by CPU 122 to be compared with the data of blood pressure in an unrest condition of the patient that is measured in a separate subsequent measurement of the patient. The CPU 122 advances the processing to S90 after S80 if it is determined that the patient was in an unrest condition.

At S90, the CPU 122 performs the processing to compare the blood pressure measured in the unrest condition with the blood pressure measured in the rest condition, which is stored in the memory 130. If the difference between the blood pressure measured in the unrest condition and the blood pressure measured in the rest condition is greater than or equal to a predetermined threshold value, the CPU 122 advances the processing to S100, and it is determined that the blood pressure of the patient is not tolerant to the unrest condition. At S100, the CPU 122 performs the processing to display on the display unit 106 the blood pressure of the patient together with an indication that the blood pressure of the patient is not tolerant to the blood pressure change affecting factor. If the blood pressure measured in the unrest condition is not different from the blood pressure measured in the rest condition by more than a threshold value, the CPU 122 advances the processing to S110, and it is determined that the blood pressure of the patient is tolerant to the unrest condition. At S110, the CPU 122 performs the processing to display on the display unit 106 the blood pressure of the patient together with an indication that the blood pressure of the patient is tolerant to the blood pressure change affecting factor.

FIG. 3 is an example of a data table that shows the blood pressure measurements, heart rates, and pulse period changes of Patient A and Patient B. According to one or more embodiments of the present invention, the data for the measured pulse period change of FIG. 3 was obtained by calculating the difference between a maximum pulse period and a minimum pulse period measured during one measurement of blood pressure by the inflation/deflation of a cuff in accordance with one or more embodiments of the present invention.

With respect to the example data table of FIG. 3, past measurements 1), 2), and 3) are shown for Patient A. According to one or more embodiments of the present invention, the data for Patient A, as shown in this table, may be compared against standard values, such as 80 beats/minute for the heart rate or 0.04 sec for the pulse period change. For example, in the past measurements of 1)-3), the difference between the measured pulse rate (81, 86, 76) and the standard value (80 beats/minute) is less than 10 beats/minute. The difference between the measured pulse period change (0.032, 0.032, 0.036) and its standard value (0.04 sec) is less than 0.02 sec. These differences of less than 10 beats/minute and less than 0.02 sec may be compared against threshold values that have been set discretionarily by the patient or a doctor in view of the common fluctuation of heart rate or pulse period values. In this example, the set threshold values are 10 beats/minute for the heart rate, and 0.02 sec for the pulse period change. Therefore, in this example, it can be said that measurements 1)-3) were each conducted when Patient A was in a rest condition.

Still referring to the example data table of FIG. 3, in the measurement of 4), the heart rate for Patient A is 101 beats/minute, which exceeds the standard value (80 beats/minute) by more than 10 beats/minute. The pulse period change is 0.104 sec, which exceeds the standard value (0.04 sec) by more than 0.02 sec. Therefore, in this example, it can be said from both data that measurement 4) was conducted when Patient A was in an unrest condition.

As shown in the example data table of FIG. 3, the difference between the systolic blood pressure value of Patient A in a rest condition, i.e., the average of 1)-3). and the systolic blood pressure value of Patient A in an unrest condition is 161−124=37 mmHg, which exceeds a threshold blood pressure value of 10 mmHg, for example. According to one or more embodiments of the present invention, the threshold blood pressure value may be set discretionarily by the patient or a doctor in view of the common fluctuation of blood pressure values.

As further shown in the example data table of FIG. 3, the difference between the diastolic blood pressure value of Patient A in a rest condition, i.e., the average of 1)-3) and the diastolic blood pressure value of Patient A in an unrest condition is 97−86=11 mmHg, which exceeds a threshold blood pressure value of 10 mmHg, for example. As previously described, according to one or more embodiments of the present invention, the threshold blood pressure value may be set discretionarily by the patient or a doctor in view of the common fluctuation of blood pressure values. Thus, with respect to both systolic and diastolic blood pressure, the blood pressure of Patient A is reacting to the unrest condition to show that Patient A is not tolerant to a change of heart rate and/or pulse period change.

According to one or more embodiments of the present invention, instead of using the standard heart rate value of 80 beats/minute, as shown in the example above, the average value of the heart rate or the pulse period change, as measured in the past measurements 1)-3) for Patient A, may be used. In that case, the standard heart rate would be (81+86+76)/3=81 beats/minute, and the standard pulse period change would be 0.032+0.032+0.036/3=0.033.
Even when these numbers are used for the standard values, the tolerance of Patient A to a change of pulse period is the same as the tolerance of Patient A to a change of heart rate.

Still referring to the example data table of FIG. 3, past measurements 5), 6), and 7) are shown for Patient B. According to one or more embodiments of the present invention, the data for Patient B, as shown in this table, may be compared against standard values, such as 80 beats/minute for the heart rate or 0.04 sec for the pulse period change. For example, in the past measurements of 5)-7), the difference between the measured pulse rate (88, 88, 88) and the standard value (80 beats/minute) is 8, which is less than 10 beats/minute. The difference between the pulse period change (0.032, 0.03, 0.048) and its standard value (0.04 sec) is less than 0.02 sec. These differences of less than 10 beats/minute and less than 0.02 sec may be compared against threshold values that have been set discretionarily by the patient or a doctor in view of the common fluctuation of heart rate or pulse period values. In this example, the set threshold values are 10 beats/minute for the heart rate, and 0.02 sec for the pulse period change. Therefore, in this example, it can be said that measurements 5)-7) were each conducted when Patient B was in a rest condition.

Still referring to the example data table of FIG. 3, in the measurement of 8), the heart rate for Patient B is 98 beats/minute, which exceeds the standard value (80 beats/minute) by 18 beats/minute. The pulse period change is 0.084 sec, which exceeds the standard value (0.04 sec) by 0.044 sec. Therefore, in this example, it can be said from both data that measurement 8) was conducted when Patient B was in an unrest condition.

As shown in the example data table of FIG. 3, the difference between the systolic blood pressure value of Patient B in a rest condition, i.e., the average of 5)-7) and the systolic blood pressure value of Patient B in an unrest condition 8) is 134−127=7 mmHg, which is below a threshold value of 10 mmHg, for example. According to one or more embodiments of the present invention, the threshold blood pressure value may be set discretionarily by the patient or a doctor in view of the common fluctuation of blood pressure values.

As further shown in the example data table of FIG. 3, the difference between the diastolic blood pressure value of Patient B in a rest condition, i.e., the average of 5)-7) and the diastolic blood pressure value of Patient B in an unrest condition is 92−87=5 mmHg, which is below a threshold value of 10 mmHg, for example. As previously described, according to one or more embodiments of the present invention, the threshold blood pressure value may be set discretionarily by the patient or a doctor in view of the common fluctuation of blood pressure values. Thus, with respect to both systolic and diastolic blood pressure, the blood pressure of Patient B is reacting to the change of heart rate and/or pulse period change to show that Patient B is tolerant to the change of heart rate/pulse period.

According to one or more embodiments of the present invention, instead of using the standard heart rate value of 80 beats/minute, as shown in the example above, the average value of the heart rate or the pulse period change, as measured in the past measurements 5)-7) for Patient B, may be used. In that case, the standard heart rate would be (88+88+88)/3=88 beats/minute. The heart rate in measurement 8) for Patient B is 98 beats/minute. Therefore, the difference between the standard heart rate and the heart rate of Patient B in an unrest condition is 98−88=10 mmHg, which is equal to the threshold of 10 mmHg. Therefore, from this data of the heart rate, the blood pressure of Patient B is tolerant to the change of heart rate.

FIGS. 4(A) and 4(B) are example displays of the data shown in FIG. 3 according to one or more embodiments of the present invention. Specifically, FIG. 4(A) shows an example display of measurement 1) of Patient A as shown in FIG. 3. FIG. 4(B) shows an example display of measurement 4) of Patient A as shown in FIG. 3.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. A blood pressure measurement device that displays a tolerance to a blood pressure change affecting factor of a patient, the device comprising:
   means for measuring blood pressure and the blood pressure change affecting factor of the patient;
   a memory that stores the measured blood pressure and the blood pressure change affecting factor;
   a tolerance determination section that determines the tolerance of the blood pressure of the patient to the blood pressure change affecting factor, the tolerance determination section further comprising:
   a rest/unrest condition determination section that:
      compares the measured blood pressure change affecting factor with a predetermined standard value;
      determines that the patient is in a rest condition if a difference between the measured blood pressure change affecting factor and the predetermined standard value is less than or equal to a predetermined threshold value; and
      determines that the patient is in an unrest condition if the difference between the measured blood pressure change affecting factor and the predetermined standard value is greater than the predetermined threshold value;
   a blood pressure tolerance determination section that:
      determines that the measured blood pressure of the patient is tolerant to the measured blood pressure change affecting factor if the difference between the measured blood pressure of the patient in the rest condition and the measured blood pressure of the patient in the unrest condition is less than a predetermined value; and
      determines that the measured blood pressure of the patient is not tolerant to the measured blood pressure change affecting factor if the difference between the measured blood pressure of the patient in the rest condition and the measured blood pressure of the patient in the unrest condition is equal to or more than the predetermined value; and
   a display unit that displays the measured blood pressure, the measured blood pressure change affecting factor, and a tolerance determination of the patient.

2. The blood pressure measurement device of claim 1, wherein the measured blood pressure change affecting factor is at least one of a heart rate and a pulse interval period of the patient.

3. The blood pressure measurement device of claim 1, wherein the display unit further displays whether the patient is in the rest condition or the unrest condition.

4. The blood pressure measurement device of claim 1, wherein the predetermined standard value is based on an average value of the measured blood pressure change affecting factor of the patient in the rest condition.

5. A blood pressure measurement device that displays a tolerance to a blood pressure change affecting factor of a patient, the device comprising:
   a cuff having an air bladder, wherein the cuff is configured to be wrapped around a measurement site of the patient;
   a measurement air system comprising a pressure sensor, a pump, and a valve;
   an air tube that connects the air bladder of the cuff to the measurement air system;
   a blood pressure calculation section that calculates a blood pressure of the patient based on an internal pressure of the air bladder as detected by the pressure sensor;
   a blood pressure change affecting factor calculation section that measures the blood pressure change affecting factor of the patient based on a detected pulse wave waveform;
   a memory that stores the calculated blood pressure and the blood pressure change affecting factor;
   a tolerance determination section that determines the tolerance of the blood pressure of the patient to the blood pressure change affecting factor, the tolerance determination section further comprising:
   a rest/unrest condition determination section that:
      compares the measured blood pressure change affecting factor with a predetermined standard value;
      determines that the patient is in a rest condition if a difference between the measured blood pressure change affecting factor and the predetermined standard value is less than or equal to a predetermined threshold value; and
      determines that the patient is in an unrest condition if the difference between the measured blood pressure change affecting factor and the predetermined standard value is greater than the predetermined threshold value;
   a blood pressure tolerance determination section that:

determines that the calculated blood pressure of the patient is tolerant to the measured blood pressure change affecting factor if the difference between the calculated blood pressure of the patient in the rest condition and the calculated blood pressure of the patient in the unrest condition is less than a predetermined value; and determines that the calculated blood pressure of the patient is not tolerant to the measured blood pressure change affecting factor if the difference between the calculated blood pressure of the patient in the rest condition and the calculated blood pressure of the patient in the unrest condition is equal to or more than the predetermined value; and a display unit that displays the measured blood pressure, the measured blood pressure change affecting factor, and a tolerance determination of the patient.

6. The blood pressure measurement device of claim 5, wherein the measured blood pressure change affecting factor is at least one of a heart rate and a pulse interval period of the patient.

7. The blood pressure measurement device of claim 5, wherein the display unit further displays whether the patient is in the rest condition or the unrest condition.

8. The blood pressure measurement device of claim 5, wherein the predetermined standard value is based on an average value of the measured blood pressure change affecting factor of the patient in the rest condition.

9. A method for measuring and displaying blood pressure using a blood pressure measurement device comprising: a processor; a memory; and a display, the processor being specifically programmed to execute the method, which comprises:

measuring by a sphygmomanometer the blood pressure of a patient together with a blood pressure change affecting factor;

determining a difference between the blood pressure change affecting factor and a standard value of the blood pressure change affecting factor;

when the difference between the blood pressure change affecting factor and the standard value of the blood pressure change affecting factor is less than or equal to a predetermined threshold value, determining that the blood pressure of the patient is measured under a rest condition, and storing the blood pressure as being measured under the rest condition in the memory;

when the difference between the blood pressure change affecting factor and the standard value of the blood pressure change affecting factor is greater than the predetermined threshold value, determining that the blood pressure of the patient is measured under an unrest condition, and comparing the blood pressure of the patient measured under the unrest condition with the blood pressure of the patient measured under the rest condition stored in the memory;

determining that the measured blood pressure of the patient is tolerant to the measured blood pressure change affecting factor if the difference between the blood pressure of the patient measured under the unrest condition and the blood pressure of the patient measured under the rest condition is less than a predetermined value;

determining that the measured blood pressure of the patient is not tolerant to the measured blood pressure change affecting factor if the difference between the blood pressure of the patient measured under the unrest condition and the blood pressure of the patient measured under the rest condition is equal to or more than the predetermined value; and displaying the measured blood pressure, the blood pressure change affecting factor, and a tolerance determination on the display of the blood pressure measurement device.

10. The method of claim 9, wherein the blood pressure change affecting factor is at least one of a heart rate and a pulse interval period of the patient.

11. The method of claim 9, further comprising displaying whether the blood pressure was measured under the rest condition or the unrest condition on the display of the blood pressure measurement device.

12. The method of claim 9, wherein the standard value of the blood pressure change affecting factor is based on an average value of the blood pressure change affecting factor of the patient in the rest condition.

* * * * *